(12) United States Patent
Buckman

(10) Patent No.: US 7,534,005 B1
(45) Date of Patent: *May 19, 2009

(54) WELDING HELMET

(76) Inventor: Michael Buckman, P.O. Box 792, Pablo, MT (US) 59855

( * ) Notice: Subject to any disclaimer, the term of this patent is extended or adjusted under 35 U.S.C. 154(b) by 113 days.

This patent is subject to a terminal disclaimer.

(21) Appl. No.: 11/707,803

(22) Filed: Feb. 13, 2007

Related U.S. Application Data

(63) Continuation-in-part of application No. 11/324,913, filed on Jan. 4, 2006, now Pat. No. 7,178,932.

(51) Int. Cl.
*F21V 21/084* (2006.01)

(52) U.S. Cl. ............... 362/105; 362/106; 362/373; 219/147; 2/8.6; 2/8.2

(58) Field of Classification Search ......... 362/105, 362/106, 373; 219/147; 2/8.2, 8.6
See application file for complete search history.

(56) References Cited

U.S. PATENT DOCUMENTS

| 3,238,535 | A | | 3/1966 | Richey |
| 3,535,707 | A | | 10/1970 | Greenlee |
| 3,649,964 | A | | 3/1972 | Schoetz |
| 3,693,748 | A | * | 9/1972 | Jones et al. ............... 181/20 |
| 4,077,007 | A | * | 2/1978 | McKinney ............... 455/142 |
| 4,109,105 | A | * | 8/1978 | Von Statten, Jr. ......... 360/92.1 |
| 4,309,774 | A | | 1/1982 | Guzowski |
| 4,641,292 | A | * | 2/1987 | Tunnell et al. ............ 367/198 |
| 4,649,571 | A | * | 3/1987 | Falkiner ................... 2/8.5 |
| 5,029,342 | A | | 7/1991 | Stein et al. |
| 5,031,237 | A | | 7/1991 | Honrud |
| 5,123,114 | A | | 6/1992 | Desanti |
| 5,561,855 | A | | 10/1996 | McFall |
| 5,896,579 | A | | 4/1999 | Johnson et al. |
| 6,242,711 | B1 | * | 6/2001 | Cooper ................ 219/130.01 |
| 7,178,932 | B1 | * | 2/2007 | Buckman ................. 362/105 |
| 2007/0056073 | A1 | * | 3/2007 | Martin et al. ............... 2/8.8 |

FOREIGN PATENT DOCUMENTS

| CA | 2184929 | 3/1998 |
| GB | 1511303 | 5/1978 |
| WO | WO81/02514 | 9/1981 |

* cited by examiner

*Primary Examiner*—Sandra L O'Shea
*Assistant Examiner*—Danielle Allen
(74) *Attorney, Agent, or Firm*—Jean Kyle

(57) ABSTRACT

Apparatus 10 disclosed an improved welders helmet having a replaceable lens 16 thereon incorporating an electrically driven fan 14 which receives filtered air through a plurality of air ducts 24 having a filter 22 thereon. A receptacle 20 for containing a battery is disposed on the helmet along with photovoltaic elements 32 for recharging the batteries from the flash of the weld. Lights 30 are also disposed on the helmet as well as communication means.

17 Claims, 12 Drawing Sheets

WELDING HELMET

CROSS-REFERENCE TO RELATED APPLICATIONS

This application is a continuation-in-part of application Ser. No. 11/324,913, filed Jan. 4, 2006 now U.S. Pat. No. 7,178,932. The disclosure of this application is hereby incorporated by reference in its entirety, including all figures, tables and drawings.

FIELD OF THE INVENTION

The present invention relates generally to protective devices and, more specifically, to an improved welders helmet incorporating means for directing airflow both internally and externally, means for filtering noxious elements from air for breathing; means for directing air within the helmet, especially across the visor; means for energizing fans incorporated into the helmet; means for recharging the power supply and selectively illuminable elements for workpiece sight enhancement; and means for communicating with fellow workers or central control.

BACKGROUND OF THE INVENTION

There are other helmet devices designed for protection. Typical of these is U.S. Pat. No. 3,238,535 issued to Richey on Mar. 8, 1966.

Another patent was issued to Greenlee on Oct. 27, 1970 as U.S. Pat. No. 3,535,707. Yet another U.S. Pat. No. 3,649,964 was issued to Schoelz on Mar. 21, 1972 and still yet another was issued on Jan. 12, 1982 to Guzowski as U.S. Pat. No. 4,309,774.

Another patent was issued to Stein, et al. on Jul. 9, 1991 as U.S. Pat. No. 5,029,342. Yet another U.S. Pat. No. 5,031,237 was issued to Honrud on Jul. 16, 1991. Another was issued to Desanti on Jun. 23, 1992 as U.S. Pat. No. 5,123,114 and still yet another was issued on Oct. 8, 1996 to McFall as U.S. Pat. No. 5,561,855.

Another patent was issued to Johnson, et al. on Apr. 27, 1999 as U.S. Pat. No. 5,896,579. Yet another U.K. Patent No. GB1511303 was issued to Kemira on May 17, 1978. Another was issued to Berg, et al. on Sep. 17, 1981 as International Patent Application No. WO81/02514 and still yet another was issued on Mar. 7, 1998 to Johnson as Canadian Patent No. CA2184929.

Richey described a welding hood having a protective front surface including a lens through which the hood user may view his work and rearwardly directed side and top surfaces formed integrally with the front surface, the improvement comprising: a transversely oriented cylindrical tube mounted across the hood side surfaces at a location adjacent the inner front surface and above the hood lens, said tube having axially open ends open respectively through apertures formed in the hood side surfaces; an electric motor mounted coaxially within said tube at the longitudinal center thereof, said motor having a driven shaft protruding axially outward at each end thereof; an pair of complementary fan blade units fixed to the motor shaft at the respective axial ends thereof, said blade units being each adapted to draw air axially toward the tube center when rotated by said motor; said tube being further provided with a lower aperture formed therethrough at the longitudinal center of the tube and directed downwardly adjacent the inside front surface of said hood; and light responsive electrical generating means mounted on the exterior of said hood and directed forwardly therefrom, said generating means being wired to said motor so as to operate said motor in response to light incident thereon.

Greenlee describes a welding helmet or the like, comprising a face shielding mask, first means for mounting said mask onto an operator's head, an opening formed through said mask, said opening being so formed as to generally forwardly directed with respect to said mask, an electrically driven motor, a fan assembly operatively, connected to said motor so as to be rotatably driven thereby, and second means carried generally within said opening and operatively connected to said mask for carrying said motor and fan assembly, said second means being effective for positioning said fan assembly in any of a plurality of varying attitudes with respect to said mask in order to enable said fan assembly to direct a stream of air in a selected direction corresponding to a selected one of said plurality of attitudes.

Schoelz describes a ventilating means for a welder's face mask employing a battery-operated blower secured on the mask. Air passageways are provided in the mask which lead from the blower to inlet openings interiorly of the mask for ventilating the area between the mask and the welder's face. Batteries for operating the blower are mounted on the head band, and in structure utilizing a mask which can be tipped up on the headband, switch means are employed between the face mask and the headband which activate the blower in the down position of the mask and deactivate the blower in the up position of the mask.

Guzowski describes a ventilating helmet which takes the form of sheet material wall member which has mounted thereon an electrically operated fan which is adapted to move air to the interior of the helmet. The electrically operated fan is to be operated through the use of a light sensitive, electrical energy producing cell. This cell is to be directly exposed to the source of light energy.

Stein et al. describe a welder's helmet including a panel of solar cells responsive to light generated by a welding operation to drive a fan incorporated in the helmet structure. The solar cells are mounted on the helmet above the viewing window and the fan is mounted in front of the mask below the viewing window. When a welding arc is struck, the light from the torch impinges on the solar panel and generates sufficient electricity to drive the fan. The fan forces air from the inside of the helmet outward through the front face in a velocity controlled stream carefully directed to prevent smoke and fumes from reaching the helmet, and to also blow the smoke away from the weld sight in a particular manner so that visibility of the weld remains clear while not over-oxygenating the weld site. As air is exhausted from the inside of the helmet outward by the fan, fresh air is drawn in around the sides to replace that which is being exhausted to cool the welder and prevent ingestion of fumes and vapors. A photovoltaic power transmission circuit is provided to process electrical energy derived from light such as that produced by the arc of an arc welder during a welding operation.

Honrud describes an apparatus and method of using a light sensitive switch, such as a photo-electric or photo-resistive cell, to actuate a battery powered electric motor which rotates a fan blade located within a housing near a facial area of a welding helmet. When exposed to a high intensity light, such as the light emitted during a welding process, the photoconductive cell actuates the battery powered motor. When activated, the motor rotates the fan blade which draws air away from the face of the wearer and passes such air through a filter into an air flow chamber, thereby, filtering the drawn air. The rotation of the fan blade then forces the filtered air toward the facial area of the wearer. A smoke block, which restricts the entrance of smoke or other contaminated vapors from entering the confines between the interior surface of the helmet and the face of the wearer, may be removably attached to the helmet.

Desanti describes a ventilated welding mask having a three chamber housing mounted thereon. A blower fan is positioned within a second medial chamber. On the rear wall of the second medial chamber, a nozzle is mounted. A conduit extends from this nozzle to an air flow manifold positioned with the welding mask.

McFall describes a welder's helmet having a plurality of photovoltaic cell panels, responsive to light produced during welding operations, for driving a pair of fans secured to opposing side walls of a head protecting shell. The photovoltaic cell panels are angularly mounted to the shell beneath a viewing window provided therein so as to permit the head of the wearer to be turned away from the welding area without affecting fan output. During operation, each of the paired fans impels air through an opening in the shell into the interior space defined by the shell. An optional battery pack, electrically connected to the fan motors provides an electrical power back-up for energizing the fans in the event that insufficient light is available to the photovoltaic panels.

Johnson et al. describe a welding helmet with an air circulating system that includes a welding hood, a head band assembly, and an air circulating system. The welding hood has an interior face receiving cavity defined by an interior helmet surface. The head band assembly being pivotally mounted to the welding helmet. The air circulating system including an air circulating assembly mounted to a top portion of the welding hood a cooling water storage bottle attached to a back portion of the head band, a wick conduit connected between the air circulating assembly and the cooling water storage bottle, a detachable battery pack housing mountable to a front structure of the air cooling assembly, and a pivotally actuation air circulating assembly on/off switch mounted between the welding hood and the head band.

Oy describes a tube with holes 4 for discharging air, closed at one end e.g. by squeezing and connectable at the other to a compressed-air hose, is used for noise suppression of air flow and direction of air flow in personal protective headgear. The tube reduces the noise level of discharging air. The tube also directs the air flow to prevent draughts and keep the front window or net of the headgear clean and dry. The straight or curved cylindrical aluminum tube is 5 to 20 mm diameter, 30 cm long and perforated by 50 round holes 4 whose diameters are from 0.7 mm to 2 mm. Gauge pressures in the tube of 0.2 kgf/cm$^2$ and 1.2 kgf/cm$^3$ produce a free air flow of 60 L/min and 170 L/min respectively. A synthetic e.g. woven nylon ribbon is wound around the tube in one or more layers or a stocking is used. The tube is attached with hose-clips to the helmet.

Berg et al. describe a powdered air respirator 10 designed to provide respiratory, eye and face protection and comprises a hard hat 11, a shell member 20 secured to the hard hat and spaced therefrom to form a generally dome-shaped passageway therebetween, air filtering means 30 in the passageway between the shell member and the hard hat, a face shield assembly 35 attached to and depending from the front of the shell member, a transparent face shield 60 in said face shield assembly, face sealing means 65 on the peripheral edge of said face shield assembly to seal against a user's face from temple to temple provided with air exits adjacent each temple and an air circulating means 70 located in the rear portion of the passageway between the shell member and the hard hat for directing a flow of air through the passageway, air filtering means, interior of the face shield assembly and out through the air exists.

Johnson describes a device for protecting a persons head while working in a hazardous environment i.e. steel industry-welding, grinding or other places where there are hazards to health (lungs, eyes and ears) and a person needs face and head protection from flying particles which may harm an individual. This invention consists of a helmet with a face shield. The helmet also consists of two (2) air filters in which each has a fan to propel air into the helmet. The fans have a rechargeable battery pack for a power source. On the bottom of the helmet is provided a piece of nonflammable material, quite soft and flexible, to provide protection to the throat and neck area from foreign material and ultraviolet rays. The helmet being made of materials designed to provide the same protection as a hard hat.

While these protective devices may be suitable for the purposed for which they were designed, they would not be as suitable for the purposes of the present invention. As hereinafter described.

All patents, patent applications, provisional patent applications and publications referred to or cited herein, are incorporated by reference in their entirety to the extent they are not inconsistent with the explicit teachings of the specification.

SUMMARY OF THE INVENTION

The present invention discloses an improved welder's helmet incorporating means for directing airflow both internally and externally, means for filtering noxious elements from the air for breathing; means for directing air within the helmet, especially across the visor; means for energizing fans incorporated into the helmet; means for recharging the power supply and selectively illuminable elements for workpiece sight enhancement. In a particularly preferred embodiment, the helmet includes audio-visual means and communication means.

A primary object of the present invention is to provide an improved welder's helmet that is versatile enough to be used in other applications by workers in dangerous or unhealthy environments.

Another object of the present invention is to provide a welders helmet comprising a housing mountable to a user's head having a viewing port with strategically placed vents, fans, lighting, in electrical communication with a portable power source.

Yet another object of the present invention is to provide a welders helmet having filter elements from removing noxious particles from air prior to inhalation.

Still yet another object of the present invention is to provide a welder's helmet having fans for directing airflow to prevent introduction of noxious fumes.

Another object of the present invention is to provide a welders helmet incorporating airflow directionals to keep the wearer cooler and prevent condensation on the view port.

Yet another object of the present invention is to provide a welders helmet having lighting elements for selectively illuminating a workpiece.

Still yet another object of the present invention is to provide a welder's helmet having a portable power source in electrically communication with said helmet.

Another object of the present invention is to provide a welder's helmet having photovoltaic elements for recharging the power source.

Additional objects of the present invention will appear as the description proceeds.

The present invention overcomes the shortcomings of the prior art by providing an improved welders helmet incorporating means for directing airflow both internally and externally, means for filtering noxious elements from air for breathing; means for directing air within the helmet, especially across the visor; means for energizing fans incorporated into the helmet; means for recharging the power supply and selectively illuminable elements for workpiece sight enhancement.

The foregoing and other objects and advantages will appear form the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and is to be understood that other embodiments may be utilized and that structural changes may be made without departing from the scope of the invention. In the accompanying drawings, like reference characters designate the same or similar parts throughout the several views.

The follow detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
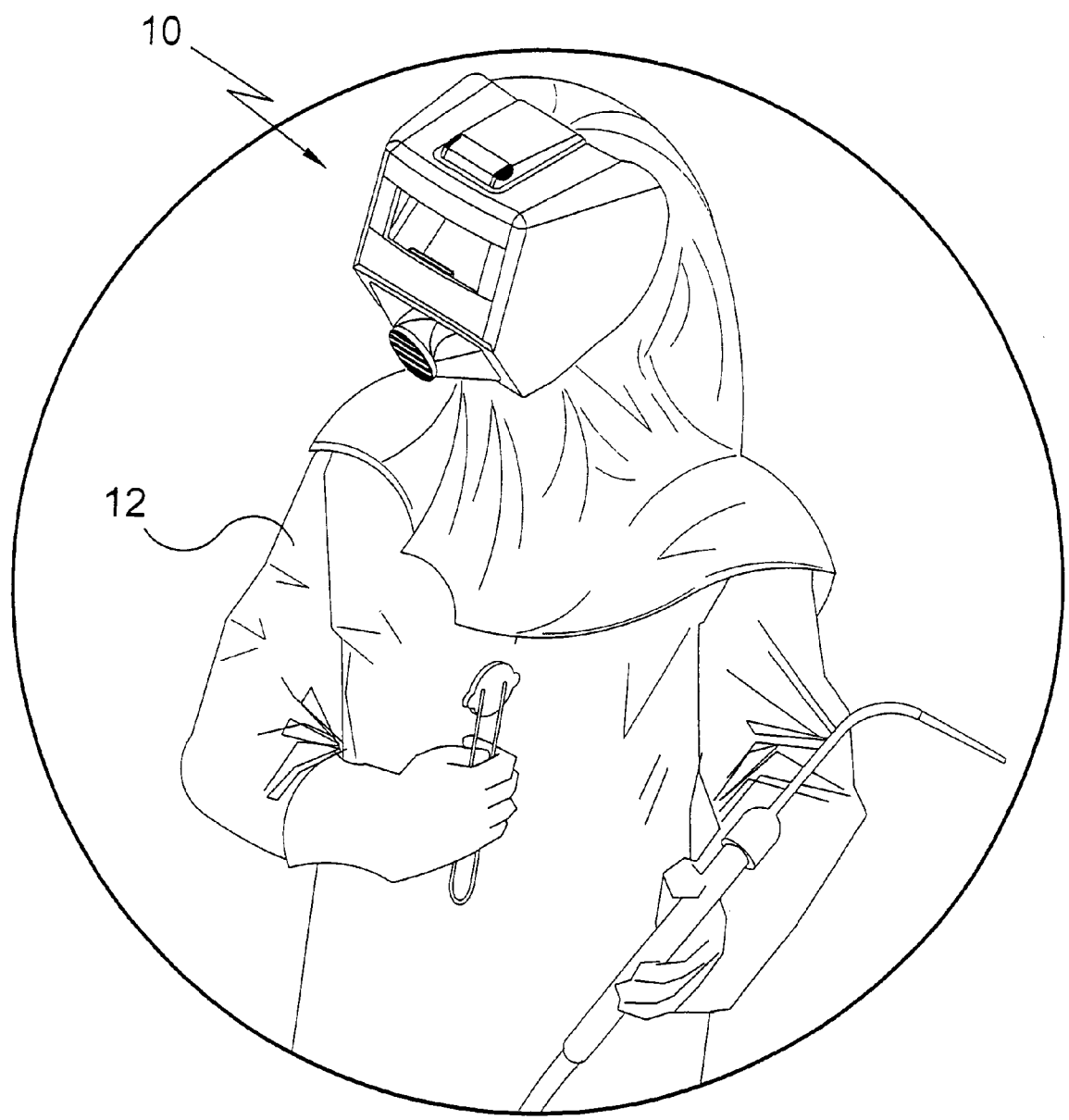
FIG. 1 is an illustrative view of the present invention in use.

With regard to reference numerals used, the following numbering is used throughout the drawings.

| | |
|---|---|
| 10 | present invention |
| 12 | welder/user |
| 14 | fan |
| 16 | lens |
| 18 | power source |
| 20 | receptacle |
| 22 | filters |
| 24 | vents |
| 26 | lower nozzle |
| 28 | blower exhaust vent |
| 30 | lights |
| 32 | photovoltaic elements |
| 34 | inlet |
| 36 | outlet |
| 38 | outlet |
| 40 | microphone |
| 42 | speaker |
| 44 | camera |
| 46 | blower |

-continued

| | |
|---|---|
| 48 | outer lens |
| 50 | inner wall |
| 52 | directional fins |
| 54 | array of LEDs |
| 56 | central control |

DETAILED DESCRIPTION OF THE INVENTION

The following discussion describes in detail one embodiment of the invention (and several variations of that embodiment). This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative view of the present invention 10 in use. The present invention 10 discloses a safer, healthier welding helmet designed to blow excessive noxious fumes and smoke away from the welder 12, and provides a plurality of fans (inner and outer) performing various tasks. The device 10 will help a welder 12 by reducing the cost of medical problems associated with breathing noxious fumes while welding.

Figure 2:
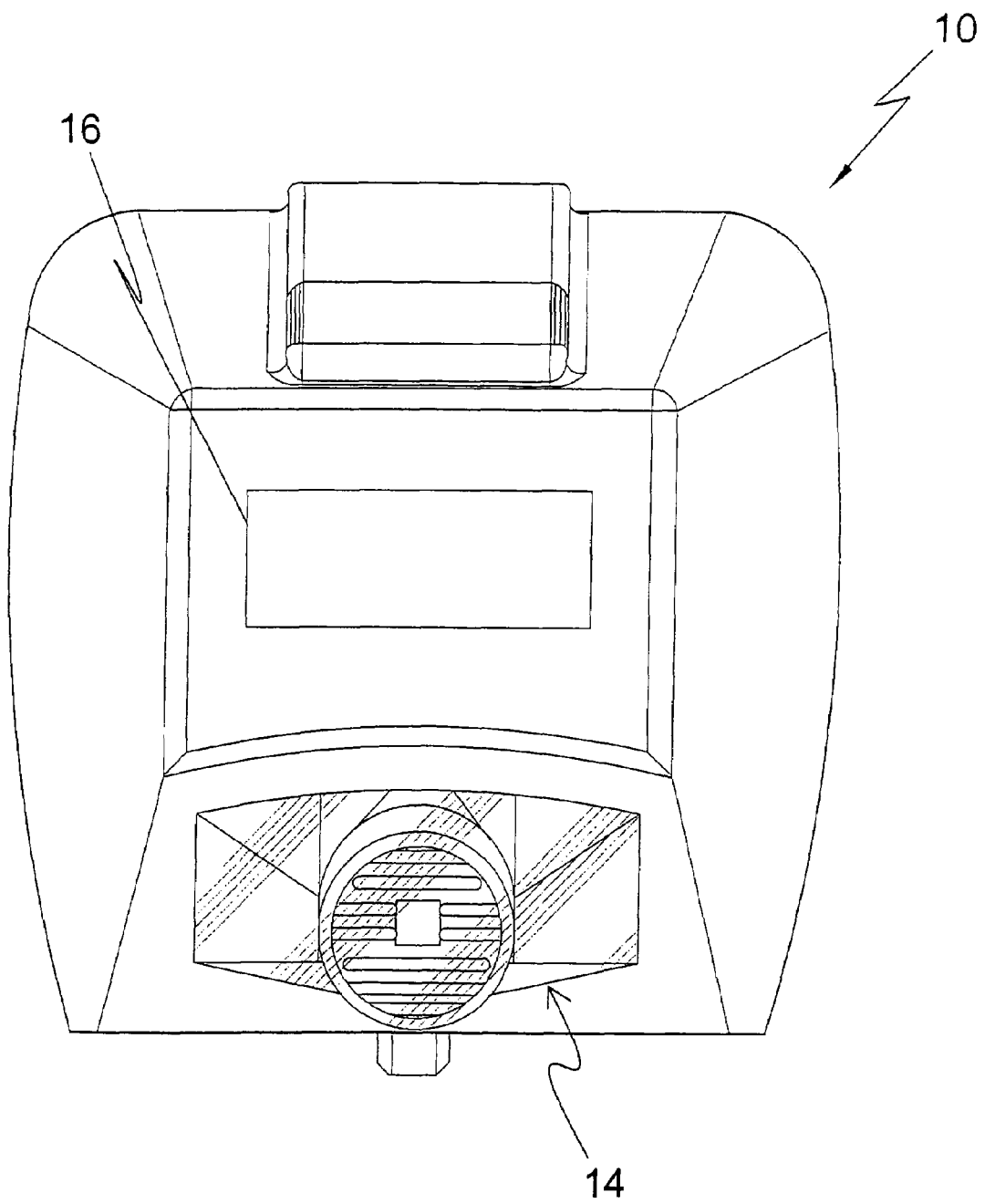
FIG. 2 is a frontal view of the present invention.
Figure 10:
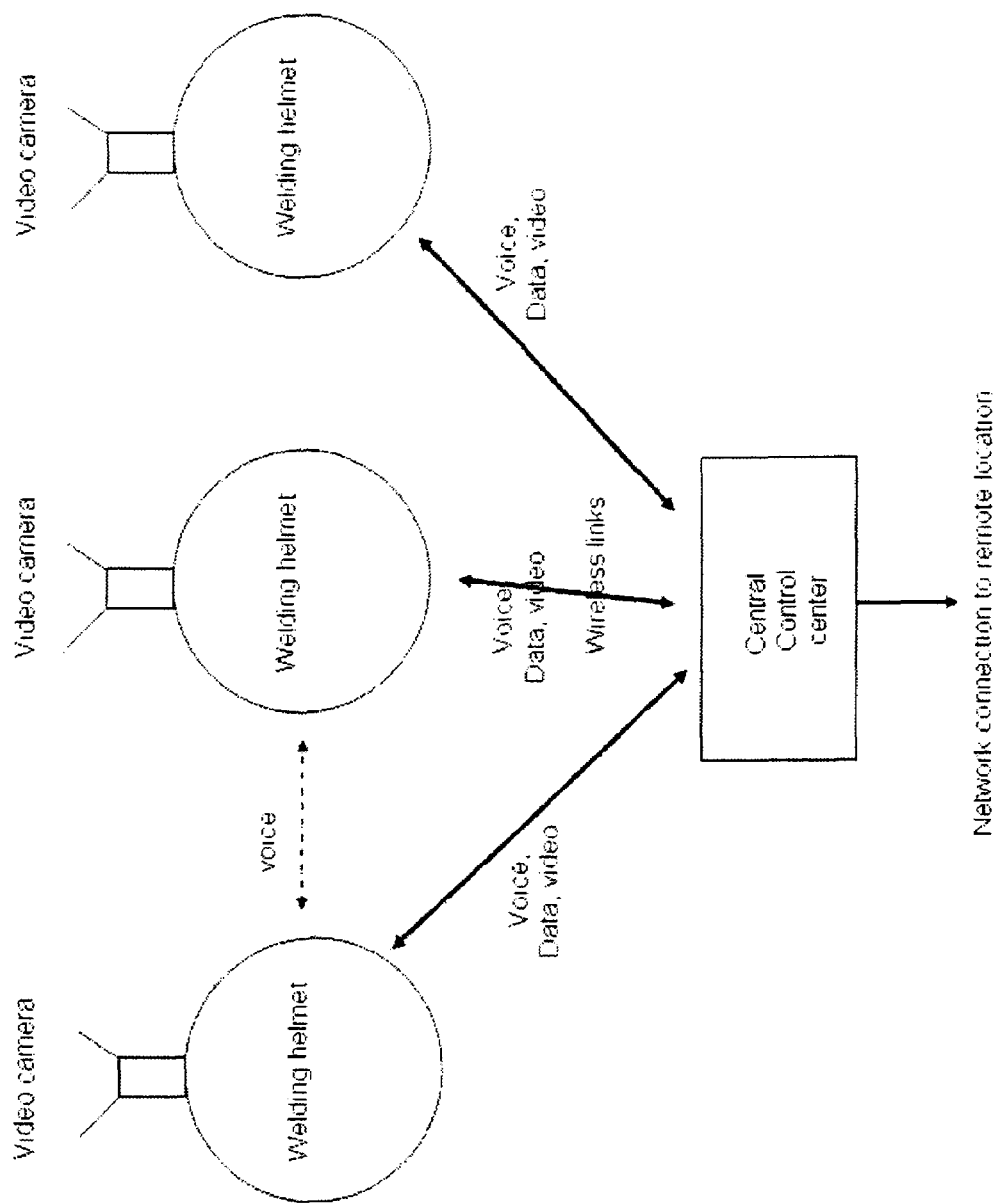
FIG. 10 is a schematic view of a preferred embodiment of a multi-user system involving the helmet of the subject invention.

Turning to FIG. 2, shown therein is a frontal view of the present invention 10. Shown is the present invention 10 and the main component of the design fan 14. The fan 14 has a single or double blade with directionals to blow noxious gases, smoke and other cancer causing fumes away from the user. There are also inner vents to keep the lens 16 from fogging, cool the welder and keep noxious gases, smoke and fumes from entering the helmet form the rear area. The welding lens 16 is replaceable with clear or other color lens for other uses such as sanding, painting, sad blasting, asbestos removal and more. A dual lens system allows the inner specialized lens 16 to be removed leaving an outer protective lens 48 so the helmet can be used in alternative applications (FIG. 10). In a particularly preferred embodiment, the external lens 48 wraps around to the side of the helmet to provide the worker peripheral vision.

Figure 3:
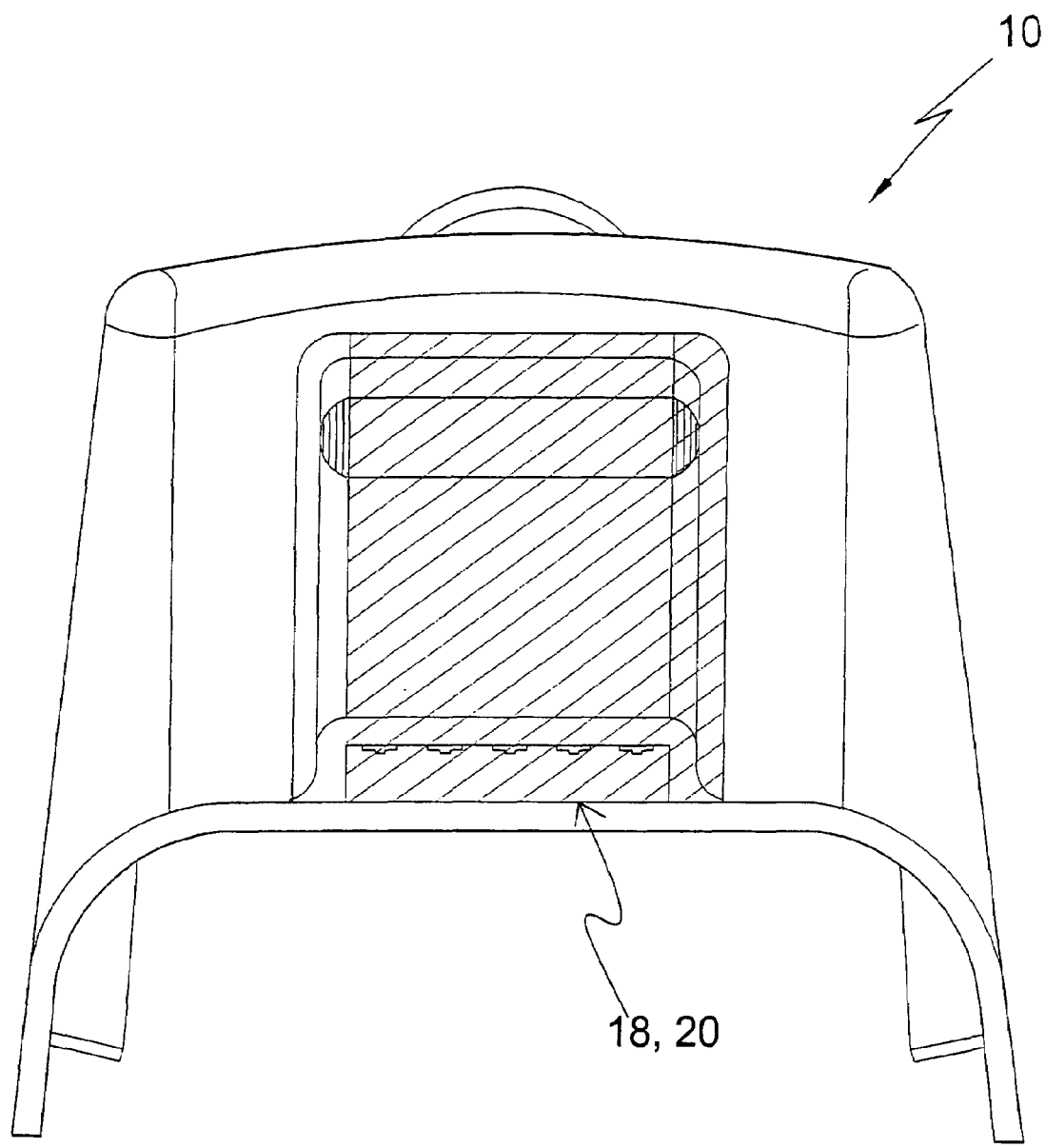
FIG. 3 is a view of the present invention.

Turning to FIG. 3, shown therein is a view of the present invention 10. This view shows the cross section area of the suggested placement of the means for receiving and applying a potential 18 to the present invention 10 which can contain the power source. In this portion the user can slide a packet of lithium ion batteries into the receptacle 20. A plurality of batteries are recommended for a longer life use. The flash of the weld using light sensitive materials can recharge the batteries. Alternatively, the power source can be dissociated from the helmet. For example, a battery pack can be carried on the belt of the wearer and connected to the helmet with a power cord. This is preferably with some power sources since the weight of these sources may be too heavy to place atop the helmet disrupting the wearer's balance and causing neck fatigue. Further, to relieve neck and shoulder fatigue a harness system can be associated with the helmet to take the weight of the helmet off the shoulders of the wearer.

Figure 4:
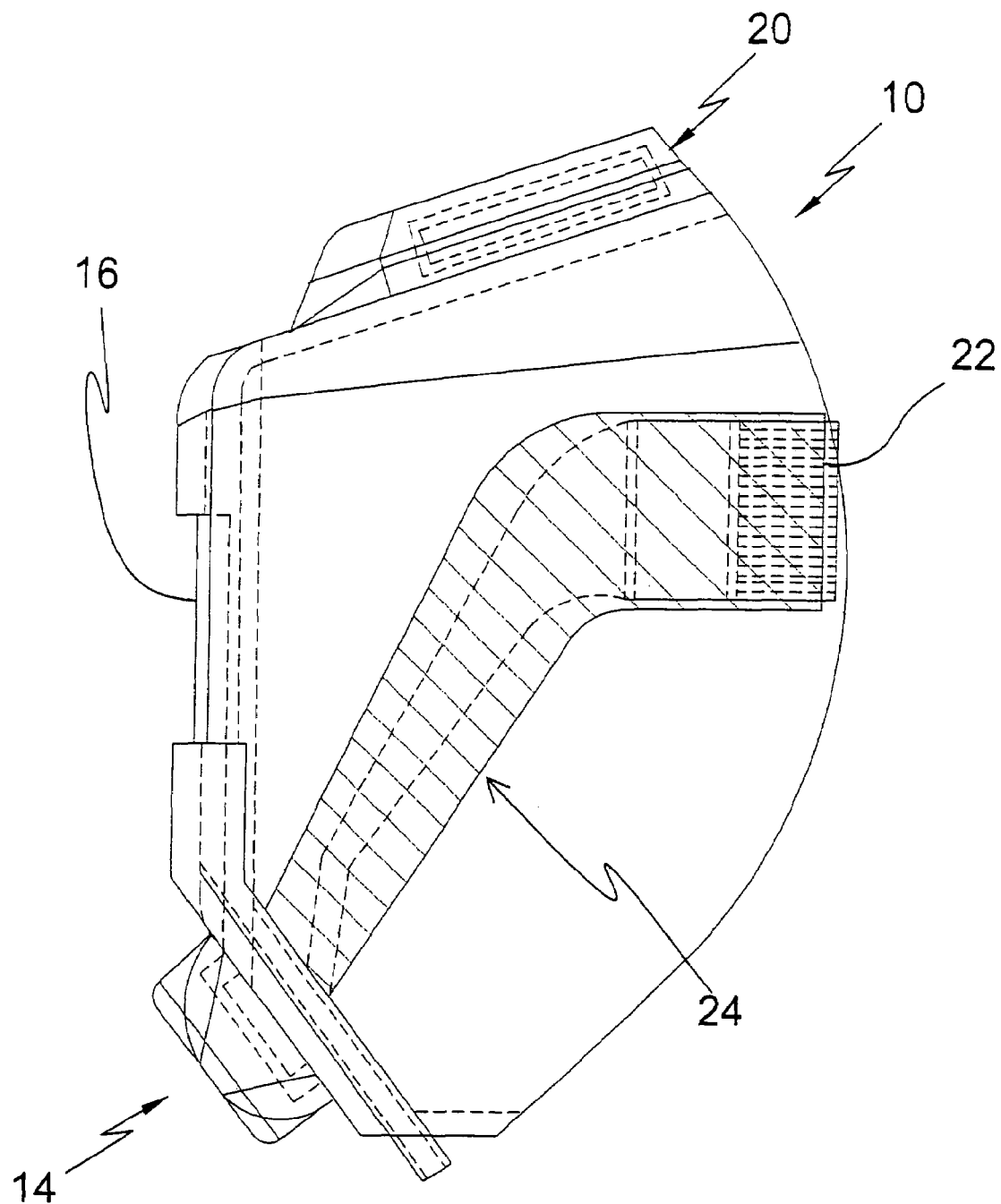
FIG. 4 is a side view of the present invention.

Turning to FIG. 4, shown therein is a side view of the present invention 10. This view shows a side view of the helmet of the present invention 10 with cross section of filters 22 and suction vents 24 and other features such as lens 16. Other previously disclosed elements are also shown.

Figure 5:
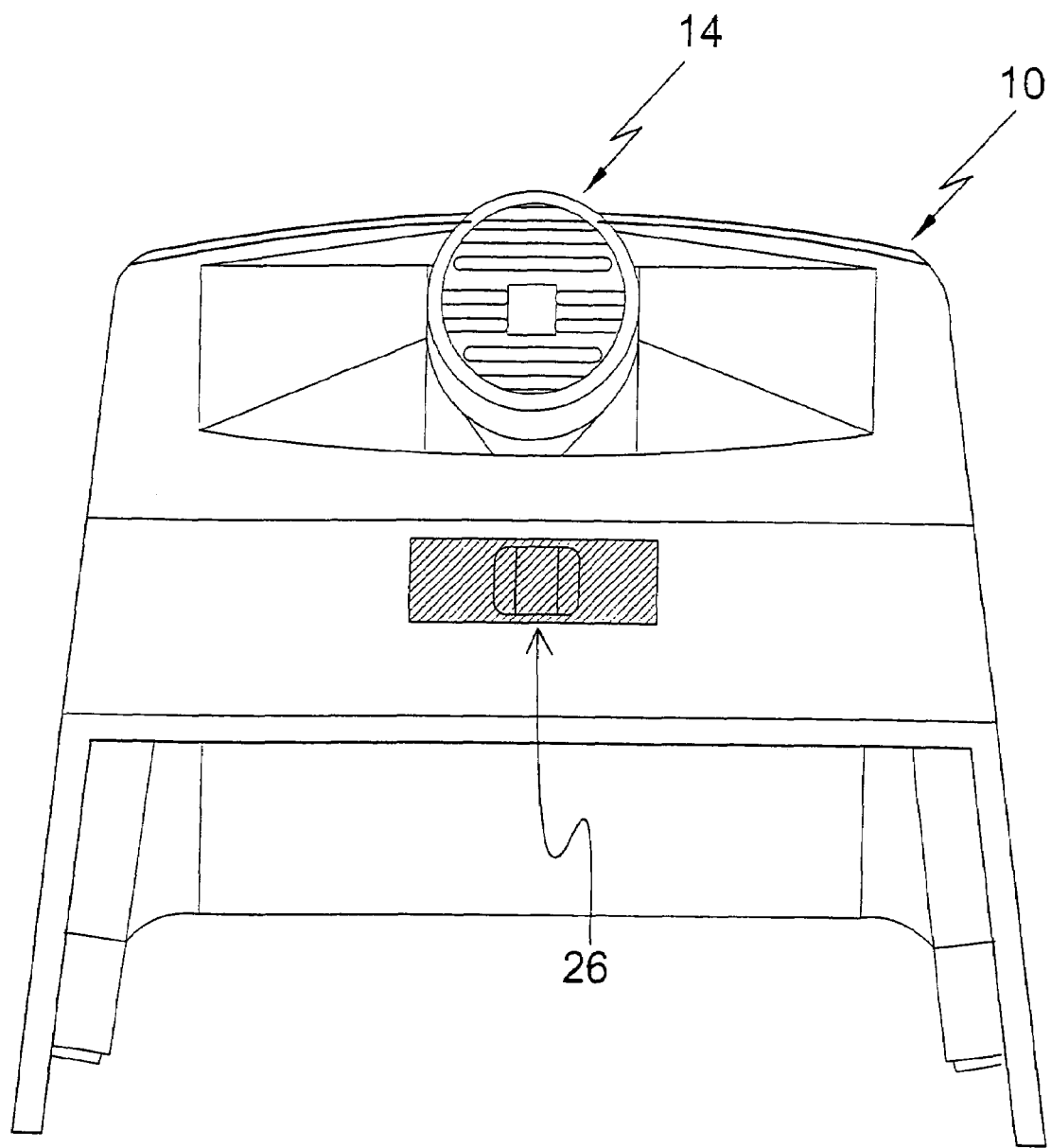
FIG. 5 is a view of the present invention.

Turning to FIG. 5, shown therein is a view of the present invention 10. This view represents the lower nozzle 26 which is as wide as the blower 14. The nozzle 26 is to hook accessory attachments, such as flat hoses in the front and rear of the user. They extend to the user's feet, if need be. This will cool the user's body in different weather conditions.

Figure 6:
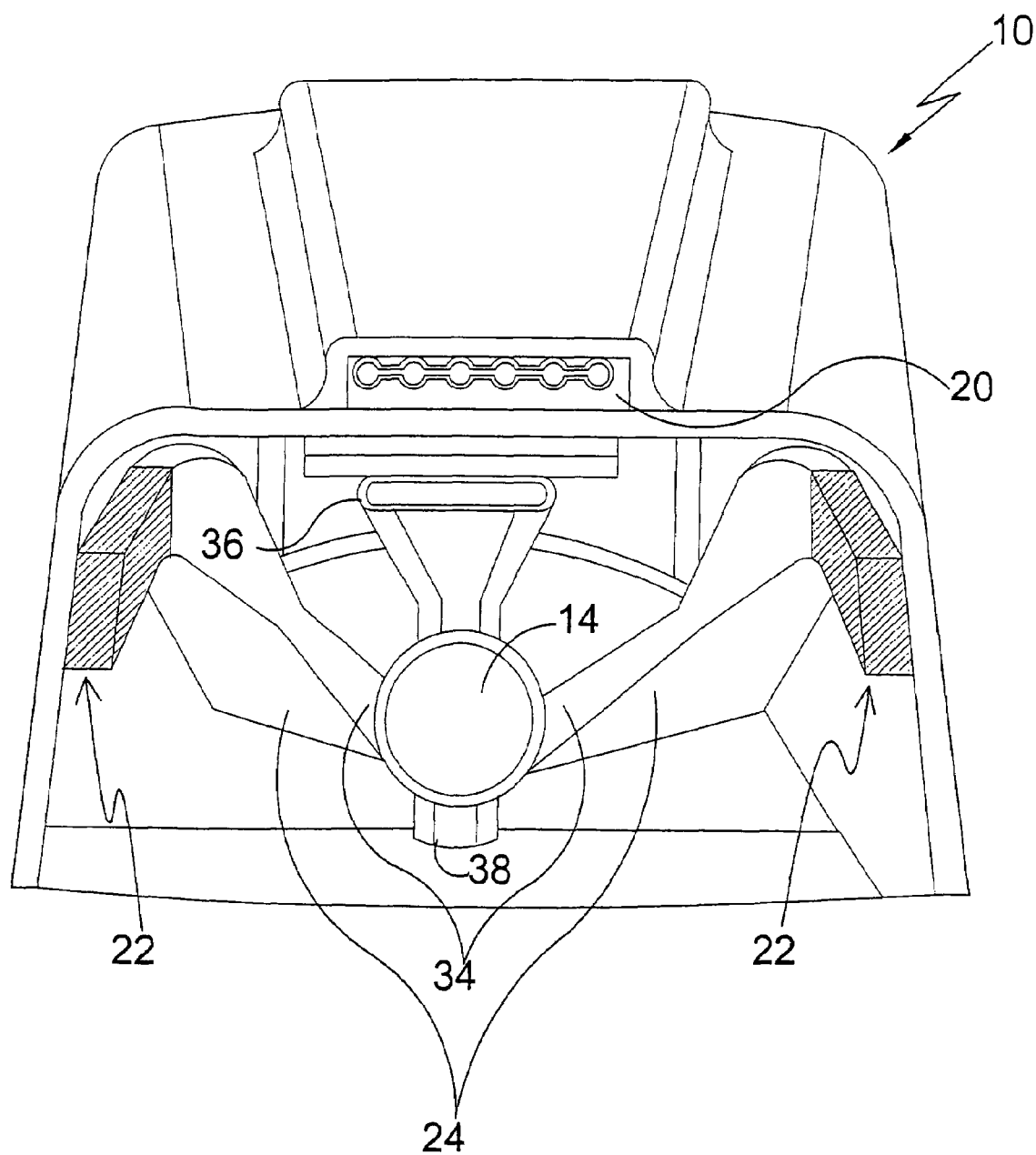
FIG. 6 is a view of the present invention.

Turning to FIG. 6, shown therein is a view of the present invention 10. This view represents the replaceable particle filter 22 HEPA filter or respirator elements that can be snapped into the suction vents to help eliminate the use of in-helmet cumbersome respirators. Also shown are the inlet 34 to the fan 4 and the first 36 and second 38 outlets from the fan along with the air ducts 24 and receptacle 20.

Figure 7:
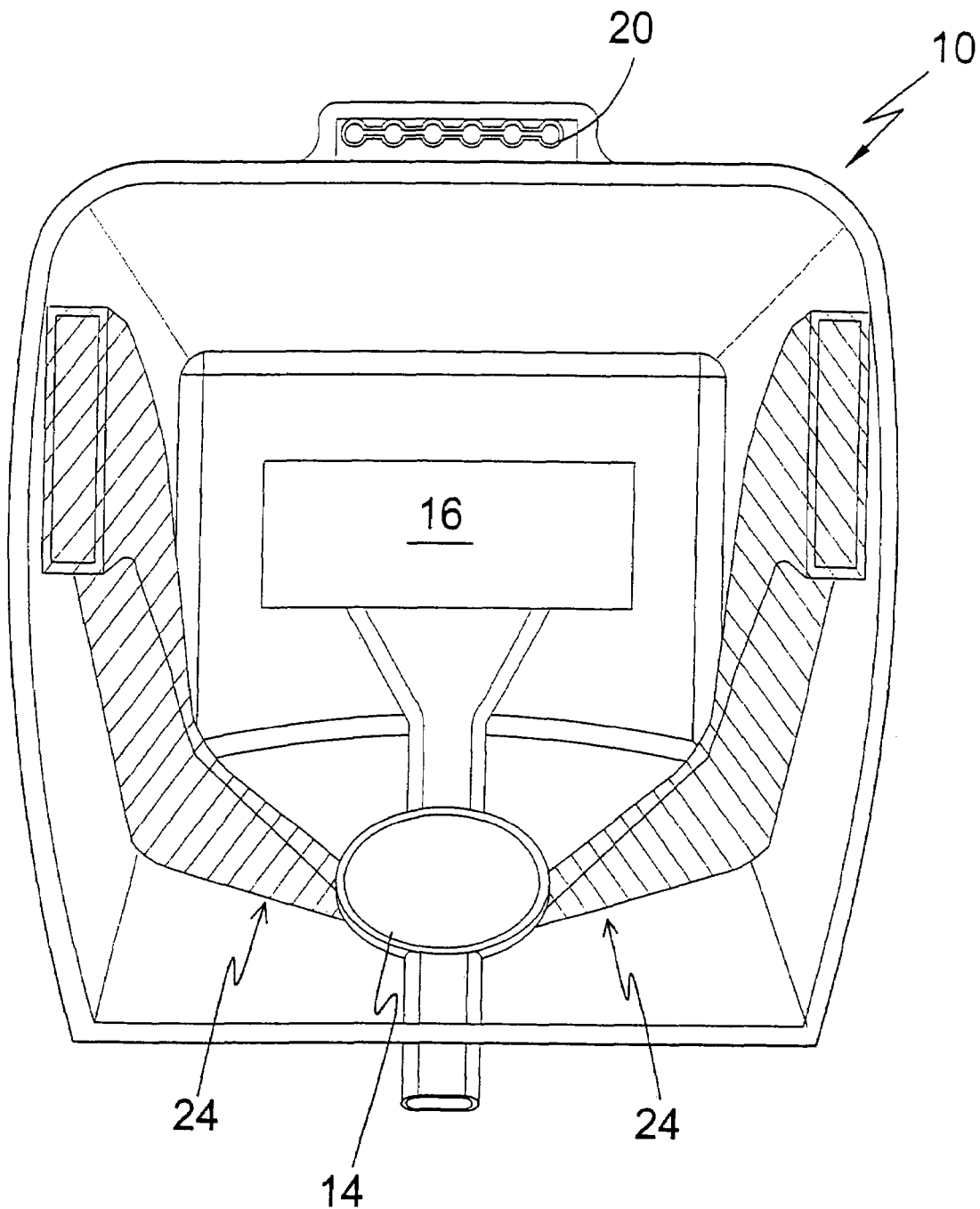
FIG. 7 is a view of the present invention.

Turning to FIG. 7, shown therein is a view of the present invention 10. This view represents the suction vents 24 that are attached to the blower 14. Also shown are lens 16 and receptacle 20.

Figure 8:
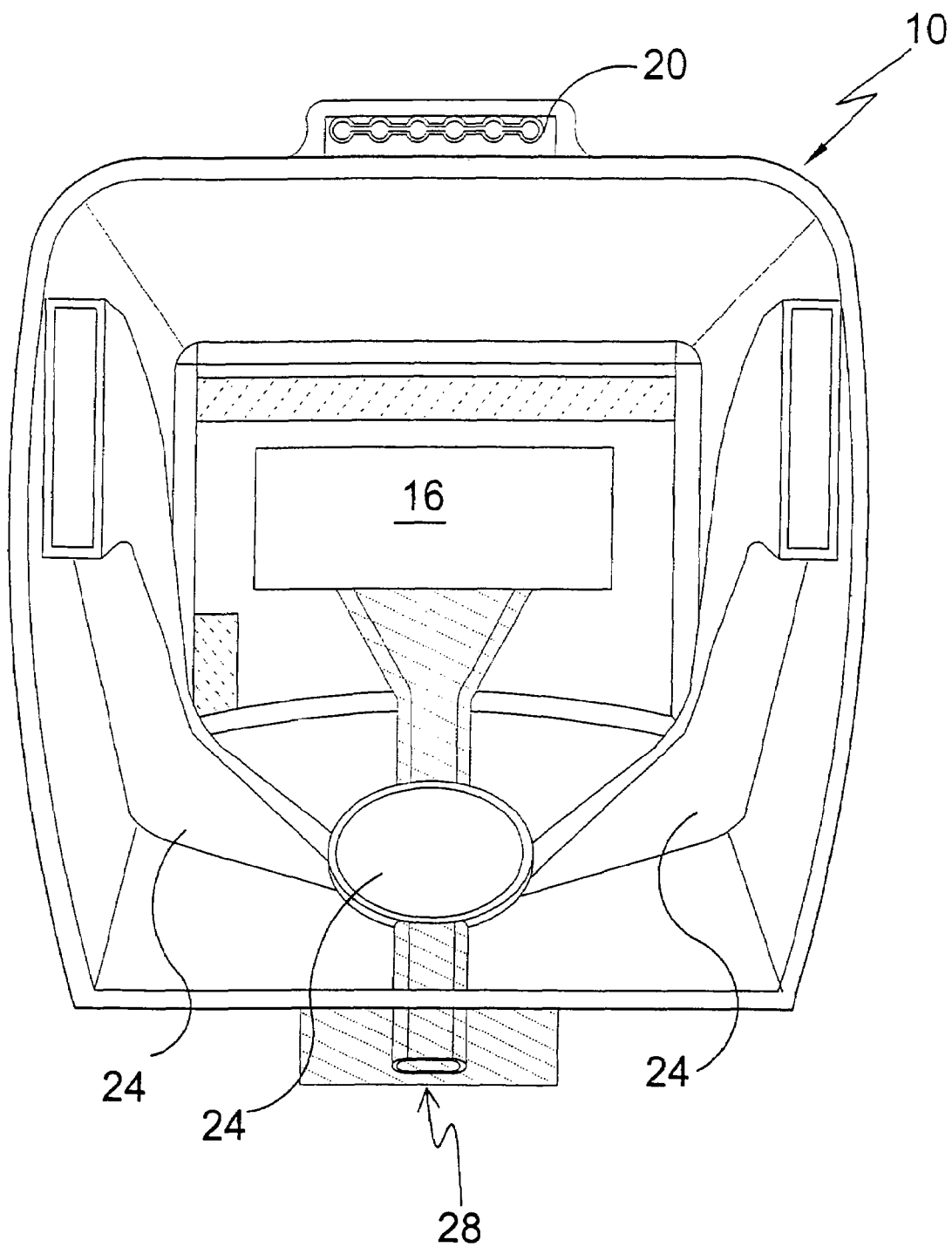
FIG. 8 is a view of the present invention.

Turning to FIG. 8, shown therein is a view of the present invention 10. This view shows the blower exhaust vents 28, these areas are suggested areas of placement for the added vents to prevent fogging, cool the user and prevent rear entry of gases, smoke and fumes. Other previously disclosed elements are also shown.

Figure 9:
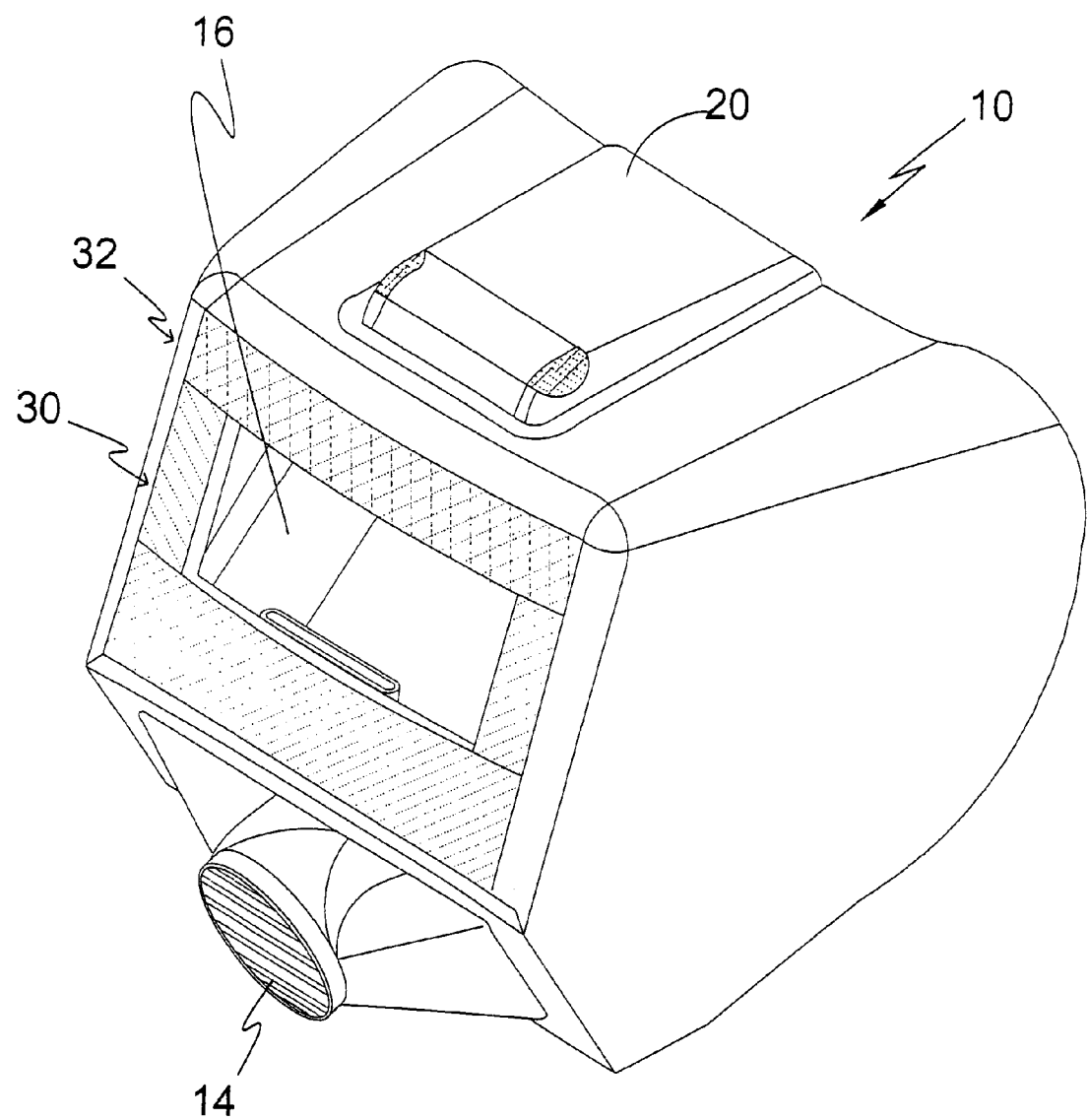
FIG. 9 is a perspective view of the present invention.

Turning to FIG. 9, shown therein is a perspective view of the present invention 10. In this view the cross section areas are bright lights 30 molded into the helmet for a better view of the work being done when welding. In a particularly preferred embodiment, an array of light emitting diodes (LEDs) 52 is used to light the work area. The double cross section represents the area where the light sensitive photovoltaic materials 32 can be placed to recharge the power sources contained in receptacle 20. The welding lens 16 is replaceable with other lens allowing the device to be used for other tasks. Also shown is fan 14.

FIG. 10 shows a preferred embodiment of a multi-user system incorporating the helmet of the subject invention. Central control 56 communicates by voice, data and video via wireless link to at least one worker 12 using the subject helmet. A suitable central control platform can include a computer, an operating system and application software. The system should included a method of multiplexing video, voice and data into a single communication system. A topology system can include point to multipoint and ad hoc. A computing platform to attach to the subject helmet can include a single board computer, an embedded processor or a commercial personal digital assistant. A suitable platform software environment can include, but is not limited to, generic OSS or low level assembly language. Input/output devices to allow the worker to communicate with central control can include a webcam, a microphone, an ear piece speaker and sensor input/output ports. Wireless technology to facilitate communication between a helmet user and central control include, but is not limited to, Wifi, BLUETOOTH, ZIGBEE and integrated computer chips.

Figure 11:
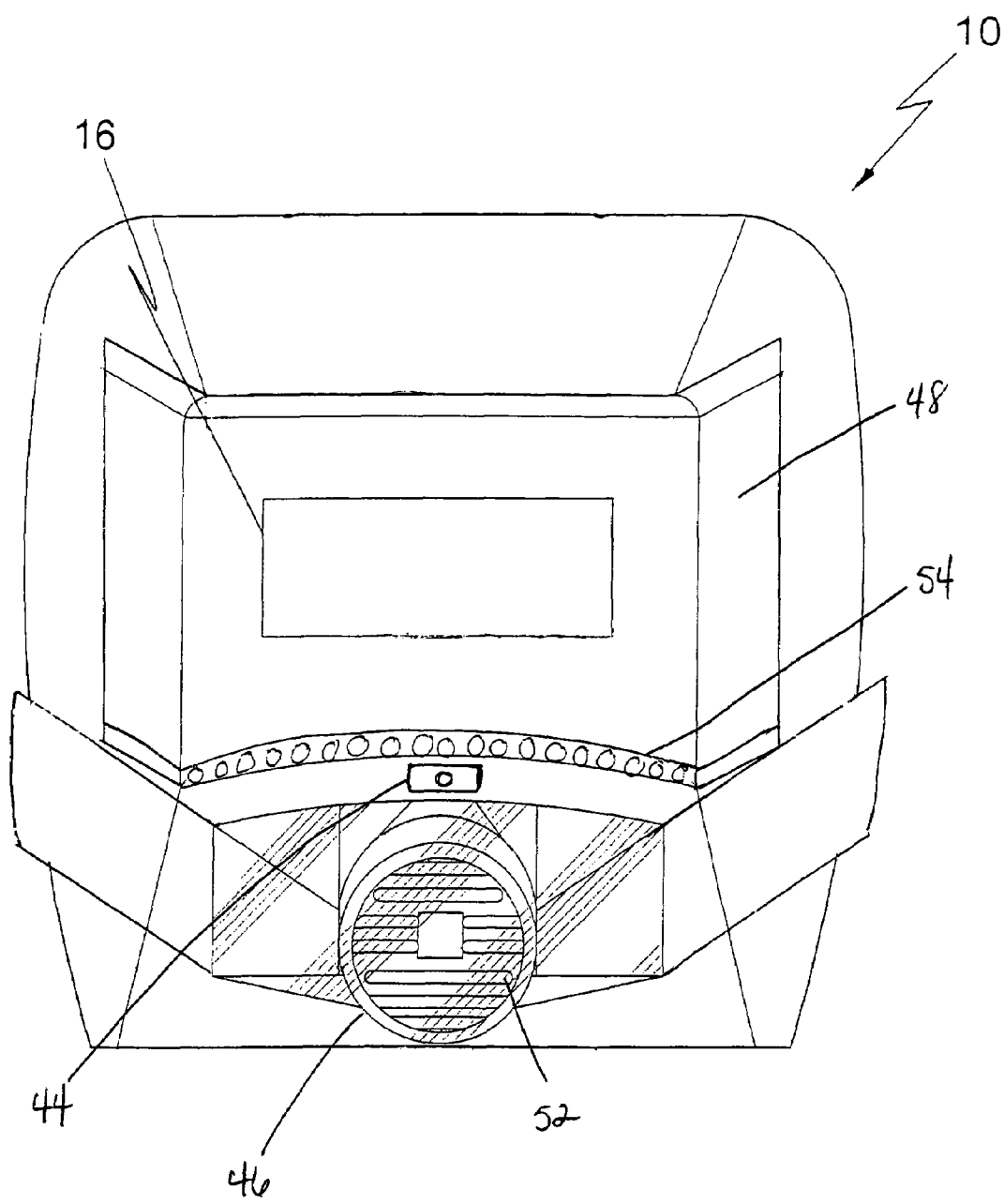
FIG. 11 is a front elevational view of another preferred embodiment of the helmet of the subject invention.
Figure 12:
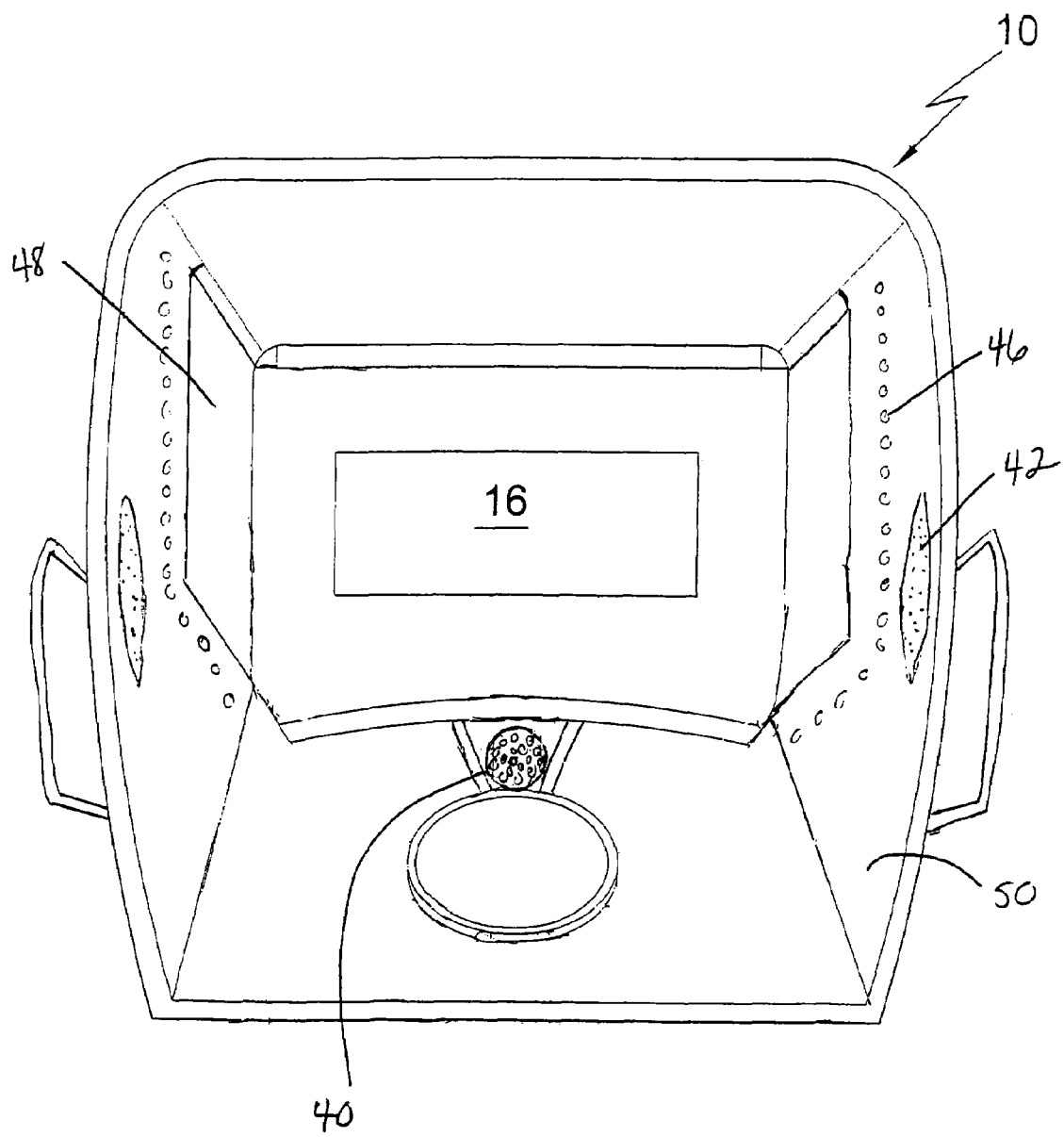
FIG. 12 is a back elevational view of another preferred embodiment of the helmet of the subject invention.

FIGS. 11 and 12 show another preferred embodiment of the helmet of the subject invention. This embodiment incorporates additional features enabling the helmet to meet the objectives of creating a healthier and safer protective helmet for a worker. In the embodiments shown in FIGS. 11 and 12, communication and audio-visual devices are included in the helmet. Simple two-way communication devices such as a walkie-talkie allow workers to communicate with one another or with a central control center without having to remove their helmets and risk exposure to harmful fumes. The helmet can also be configured to send environmental and bio sensor data to a control center. Further, the helmet can be configured to use a local wearable computer to display drawings, instruction and other information pertaining to the wearer's task.

Simple, lightweight components should be used to provide audio/visual capabilities to the helmet of the subject invention. Preferably, the components are battery powered and have a minimum number of controls to operate. The system must operate over a distance to accommodate worker to worker communication as well as worker to control center communication. It is particularly preferred that the audio or audio/visual communication system support multiple users simultaneously in communication with central control and that central control can connect to an external network to enable remote access. The helmet can incorporate a simple microphone 40 and speaker 42. The helmet can also be configured to receive and transmit remote communications via cell phone. When used in association with a video device such as a camera 44, the subject helmet not only protects the worker but persons associated with the worker. For example, welding instructors can supervise the work of their students via remote monitor removing themselves from harmful and irritating fumes. Welds can be inspected remotely preventing an inspector from placing themselves in danger by having to, for example, climb high into the frame of a steel building. Communication to a worker can also be directed via a heads-up display.

In the helmet shown in FIGS. 11 and 12 the wall of the helmet is two layers. Air circulated by the helmet is directed through air vents holes 46 in the inner wall 50. Distribution of the air through these vents more evenly distributes the circulated air and prevents discomfort of the wearer from the excessive force of the air near its source. The air vent holes 46 create a positive pressure within the helmet preventing outside air and noxious fumes form entering. Dual wall construction allows auxiliary components to be recessed in the wall or encased in the helmet shell, for example, a heating element (not shown) to warm the air in the helmet.

An additional fan or blower 48 is added to the embodiment shown in FIGS. 11 and 12. The blower 48 is mounted on the exterior of the helmet and blows air away from the helmet to clear the work area of smoke. The external fan 48 is unfiltered and does not provide air to the user. This fan or blower can supplement or replace the exhaust for the inner fan. The fan can further have directional fins 52 so the user can direct the airflow. Additionally, the fan can have variable speed control to allow the user to slow or cease exhaust from the fan to save power. Preferred for use for the both inner and outer blowers are CPU fans. Theses fans are small, provide good quantities of air and draw very little power.

Fans and blowers of the subject invention can include additional booster or pre-fans to assist in drawing or expelling air from the helmet. Further, filters to clean the air drawn into the helmet can likewise have pre-filters. For example, a particle filter can precede a gas filter to prolong life of the more expensive gas filter. Filters contemplated for use in the subject invention include dual density filters alone or in combination with felt based wet/dry type filters for capturing smaller particles and ultimately pleated gas filters.

Although the subject helmet has been described primarily for use by a welder, the helmet is useful in many other situations. The helmets can be used in search and rescue situations at chemical spills or during a fire. Further the helmets can be used in industries where toxic adhesives or accelerants are used.

It is understood that the foregoing examples are merely illustrative of the present invention. Certain modifications of the articles and/or methods employed may be made and still achieve the objectives of the invention. Such modifications are contemplated as within the scope of the claimed invention.

I claim:

1. An apparatus for a self-contained welding helmet, comprising:
   a) a helmet for being mounted on the head of a user, said helmet having a front wall having upper and lower portions, a pair of laterally spaced side walls and a top extending rearwardly from said front wall defining an interior space adapted to receive the head of a user therein, said side walls having a rear end;
   b) a lens being disposed on said front wall of said helmet so that a user can see through said lens, wherein said lens can be removed from said wall and replaced in said wall;
   c) a first fan having an electrical drive motor thereon for directing airflow about said helmet, said fan having an air inlet port and at least one air exhaust port;
   d) a second fan having an electrical drive motor thereon being disposed on said front wall of said helmet for directing airflow away from the helmet;
   e) a plurality of air ducts having first and second ends being disposed on said interior of said helmet so that said first end is connected to said air inlet port of said fan and said second end is disposed on each said side wall proximate said rear end of said side wall so that air enters said second end of said air duct wherein the air is drawn toward said fan;
   f) at least one air filter being disposed on said second end of each said air duct so as to filter the air being drawn toward said fan;
   g) wherein said at least one air exhaust port is adapted to blow air across said lens so that said lens is kept free of condensation;
   h) a plurality of lights being disposed on said helmet so that a workspace can be lighted; and
   i) means for receiving and applying a potential to said electrical drive motor and said lights whereby the electrical drive motor and lights can be energized.

2. The apparatus of claim 1, further comprising communication means.

3. The apparatus of claim 2, wherein said communication means is selected from the group consisting of audio communication means, video communication means and data communication means.

4. The apparatus of claim 1, further comprising audio communication means and video communication means.

5. The apparatus of claim 1, wherein said air duct comprises more than one filter.

6. The apparatus of claim 1, wherein said helmet comprises another lens.

7. The apparatus of claim 1, wherein said walls have a dual wall assembly.

8. The apparatus of claim 1, further comprising central control means remote from and in communication with said helmet.

9. The apparatus of claim 8, wherein said central control means and said helmet are in audio communication.

10. The apparatus of claim 8, wherein said central control means and said helmet are in video communication.

11. The apparatus of claim 8, wherein said central control means and said helmet are in data communication.

12. The apparatus of claim 8, wherein communication is wireless.

13. A multi-user system comprising:
    at least one self-contained welding helmet, the helmet comprising;
       a) a helmet for being mounted on the head of a user, said helmet having a front wall having upper and lower portions, a pair of laterally spaced side walls and a top extending rearwardly from said front wall defining an interior space adapted to receive the head of a user therein, said side walls having a rear end;
       b) a lens being disposed on said front wall of said helmet so that a user can see through said lens, wherein said lens can be removed from said wall and replaced in said wall;
       c) a first fan having an electrical drive motor thereon for directing airflow about said helmet, said fan having an air inlet port and at least one air exhaust port;
       d) a second fan having an electrical drive motor thereon being disposed on said front wall of said helmet for directing airflow away from the helmet;
       e) a plurality of air ducts having first and second ends being disposed on said interior of said helmet so that said first end is connected to said air inlet port of said fan and said second end is disposed on each said side wall proximate said rear end of said side wall so that air enters said second end of said air duct wherein the air is drawn toward said fan;
       f) at least one air filter being disposed on said second end of each said air duct so as to filter the air being drawn toward said fan;
       g) wherein said at least one air exhaust port is adapted to blow air across said lens so that said lens is kept free of condensation;
       h) a plurality of lights being disposed on said helmet so that a workspace can be lighted; and
       i) means for receiving and applying a potential to said electrical drive motor and said lights whereby the electrical drive motor and lights can be energized; and
    a central control remote from and in communication with the helmet.

14. The system of claim 13, wherein said at least one helmet and said central control communicate by a means selected from the group consisting of audio communication means, video communication means and data communication means.

15. The system of claim 14, wherein said communication means are wireless.

16. The system of claim 13, comprising at least two helmets configured for audio communication between the helmets.

17. The system of claim 13, wherein said central control is connectable to an external network.

* * * * *